United States Patent [19]

Knifton

[11] Patent Number: 5,177,301

[45] Date of Patent: Jan. 5, 1993

[54] METHOD OF SEPARATING ISOBUTYLENE FROM A C-4 HYDROCARBON FRACTION USING A HETEROPOLY ACID ON AN INERT SUPPORT

[75] Inventor: John F. Knifton, Austin, Tex.

[73] Assignee: Texaco Chemical Company, White Plains, N.Y.

[21] Appl. No.: 822,803

[22] Filed: Jan. 21, 1992

[51] Int. Cl.⁵ .................. C07C 7/148; C07C 7/17
[52] U.S. Cl. .................. 585/855; 585/313; 585/324; 585/639; 585/868; 568/697
[58] Field of Search ............... 585/310, 312, 313, 836, 585/866, 639, 324; 568/697

[56] References Cited

U.S. PATENT DOCUMENTS

| | | | |
|---|---|---|---|
| 4,259,533 | 3/1981 | Guttman et al. | 568/697 |
| 4,320,232 | 3/1982 | Volkamer et al. | 585/639 |
| 4,376,219 | 3/1983 | Murofushi et al. | 568/697 |
| 4,570,026 | 2/1986 | Keyworth | 585/312 |

*Primary Examiner*—Anthony McFarlane
*Attorney, Agent, or Firm*—Jack H. Park; Kenneth R. Priem; Cynthia L. Kendrick

[57] ABSTRACT

Disclosed is a two-step method for separating isobutylene from a C-4 hydrocarbon fraction comprising:

a) Reacting the C-4 fraction with a glycol in the presence of a catalyst comprising heteropoly acid on an inert support at a temperature of about 60° to 160° C. to yield the corresponding glycol mono-t-butyl ether, and subsequently b) reacting the intermediate glycol ether product over the same class of catalyst at a temperature of about 100° to 220° C. to regenerate the isolatable isobutylene.

12 Claims, No Drawings

1

METHOD OF SEPARATING ISOBUTYLENE FROM A C-4 HYDROCARBON FRACTION USING A HETEROPOLY ACID ON AN INERT SUPPORT

FIELD OF THE INVENTION

This invention relates to the separation of isobutylene from a C-4 hydrocarbon fraction. More particularly this invention relates to a two-step method of separating isobutylene from a C-4 hydrocarbon fraction using as a catalyst a heteropoly acid on an inert support.

BACKGROUND OF THE INVENTION

Separation of olefins from mixed hydrocarbon streams has long been a subject of research and process development efforts. This field includes such widespread applications as recovery of ethylene from steam cracker effluents or dilute refinery streams, $C_2$ and $C_3$ splitting, and recovery of butene-1 from mixed C-4 streams. One of the valuable olefins which can be separated out of a C-4 hydrocarbon stream is isobutylene. Isobutylene is valuable, among other uses, as a reactant in the preparation of high octane ethers such as methyl t-butyl ether and ethyl t-butyl ether, as well as ethylene and propylene glycol ethers.

In Chem Systems, Topical Reports, Vol. II, p. 1 (1988 Program), September 1989 there is discussed the recovery of butene-1 by complexation.

The use of complexing agents in solution for complexation of olefins to separate them from paraffins is addressed in U.S. Pat. Nos. 3,401,112 and 3,449,240 to Shell. Other patents describe olefin-paraffin separation by means of a selective complex formation. See U.S. Pat. Nos. 3,517,080 and 3,517,081 to Monsanto.

Research has demonstrated the removal of ethylene from dilute streams with cuprous containing complexes in aromatic solvents. See U.S. Pat. Nos. 3,592,865; 3,651,159 and 3,754,047 to Esso Research and Engineering. To review additional research in this area, see Gottesman, R. T. "A New Process for Separation of Ethylene from Low Grade Gas Streams," Technology Exchange, Chicago, Ill. (February 1977) and Gutierrez, A. P. et al. "ESEP-A Process for the Recovery of Ethylene" paper presented at the 175th ACS Meeting, Anaheim, Calif. (Mar. 12-17, 1978). An attractive process for ethylene recovery from a cat cracker off-gas was reviewed in Chem. Systems, PERP Third Quarterly Report, Section 3.00 (1978). Other complexing solutions and complexing agents incorporated into solid adsorbents and membranes are disclosed in U.S. Pat. No. 3,828,398 to Esso, U.S. Pat. No. 4,025,574 to Phillips, U.S. Pat. No. 4,545,966 to Walker and U.S. Pat. No. 3,979,280 to Deutsche Texaco.

In an article by Ho, N. S., Winston, Doyle, G., Savage, D. S. and Pruett, R. L. I.E.C. Res. 1988, 27, p. 334, there is described the use of a complexing solution for the separation of $C_2$-$C_5$ olefins and linear $\alpha$-olefins from internal and branched olefins of the same carbon number. The complexing solution is covered in U.S. Pat. No. 4,471,152 to Esso.

In the Chem Systems, Topical Reports, Vol. II reference above at page 4, it is indicated that the complexing solution of U.S. Pat. No. 4,471,152 works best for separating ethylene and in the last paragraph there is reference to the "suppression of the complexation of internal and branched olefins." Therefore this technology teaches away from benefits in attempting to separate isobutylene. This technology is of special interest in the separation of $\alpha$-olefins and, thus, more separation is expected of butene-1 and butene-2. In Section 1.22, Ibid, there is a description of the application of copper complexation technology to recovery of butene-1 from a steam cracker C-4 stream. At page 7, last paragraph it is stated this technology is selective for butene-1 compared to isobutylene and all other C-4 components.

At subtitle 1.31 on page 10, Ibid, it is stated "isobutylene and butadiene are seen to be virtually inseparable from butene-1." Technologies are discussed for butene-1 recovery.

J.P. 59,051,224-A (to Maruzen) discloses isobutylene separation from C-4 hydrocarbon distillate fraction by countercurrent reaction with ethylene glycol in the presence of a cation exchange catalyst.

In related copending applications, Ser. Nos. 07/396,209 and 07/410,168 incorporated herein in their entirety by reference, methods are described for the preparation of ethylene and propylene glycol ethers from isobutylene and the corresponding glycol over an acidic montmorillonite clay catalyst or an acidic heterogeneous or homogeneous catalyst.

J.P. 55,053,228 discloses a method for the preparation of ethylene glycol tertiary-butyl ether by reacting ethylene glycol with isobutylene in the presence of a strongly acidic cation exchange resin.

In J.P. 63,250,336 there is described a method for the preparation of propylene glycol tert-butyl ether by reacting propylene glycol with isobutylene in the presence of a strong acidic cation-exchange resin and tert-butanol.

The separation of particular components of C-4 streams such as isobutylene, butene-1, 1,3-butadiene, etc. in good yield and purity is obviously a desirable goal in the art. It would be especially helpful if it were possible to separate isobutylene using an efficient, commercially attractive process. The isobutylene isolated could be used to produce valuable solvents such as propylene glycol and ethylene glycol monobutyl ethers.

There does not appear to be any art suggesting the separation of isobutylene from a C-4 hydrocarbon fraction using a heteropoly acid on an inert support.

It has been discovered that heteropoly acid on an inert support such as titania can be used to separate isobutylene from a C-4 fraction in two steps. It is an object of the present invention to separate isobutylene in good yield and regenerate glycol. Other objects will become apparent to those skilled in the art from the following description.

SUMMARY OF THE INVENTION

In accordance with the foregoing, the novel method of this invention for separation of isobutylene comprises reacting a C-4 rich hydrocarbon stream containing the isobutylene fraction with a glycol over a catalyst comprising a heteropoly acid on an inert support in order to etherify the isobutylene fraction; and subsequently reacting the intermediate over the same class of catalyst at a higher temperature to give pure isobutylene and regenerated glycol.

DESCRIPTION OF THE PREFERRED EMBODIMENT

The separation of isobutylene in the instant invention may be carried out by reacting a C-4 hydrocarbon fraction in the presence of a catalyst comprising a heteropoly acid on an inert support.

The method requires two steps which comprise:
1) Etherification of the isobutylene fraction of said C-4 stream (e.g. raffinate-1) with a glycol, such as, for example, ethylene glycol or 1,2-propylene glycol over a heteropoly acid on an inert support to give the corresponding glycol mono-t-butyl ether, and
2) deetherification of the glycol t-butyl ether intermediate to give pure isobutylene plus regenerated glycol by reaction at higher temperature over the same class of supported heteropoly acid catalyst.

This can be represented for the intermediate synthesis of ethylene glycol t-butyl ether by the following equation:

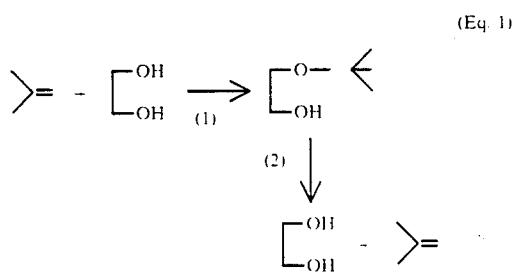

(Eq. 1)

The glycols which are useful in the practice of this invention are generally diols having 2 to 20 carbon atoms per molecule. They may include vicinal glycols where the hydroxyl groups are bonded to adjacent carbon atoms, as in Eq. 1, or alternatively, the hydroxyl groupings may be separated by additional carbon atoms, as in the case of 1,3-propylene glycol and 1,6-hexane diol. Alternatively, said substrates may contain three or more hydroxyl groups per molecule, as in the case of glycerine, or they may be a polyalkylene glycol, particularly a polyethylene glycol or a polypropylene glycol containing multiple ether linkages and terminal hydroxyl groups. Said polyalkylene glycols may have molecular weights in the range of from ca. 150 to ca. 6000, and be mixtures of different polyethylene glycol or polypropylene glycol oligomers. Furthermore they may be capped or contain within the backbone, certain higher molecular weight carbon units, such as the C-4 unit, introduced during oligomerization by the addition of, for example, 1,2-butylene oxide or isobutylene oxide.

The preferred glycols for the separation of isobutylene by etherification/deetherification using a heteropoly acid on an inert support are ethylene glycol or 1,2-propylene glycol.

The molar ratio of said glycols to isobutylene in said C-4 hydrocarbon fraction in the feed mixture may vary widely, from 1:1 to 1000:1. To achieve optimum selectivities and yields of separated isobutylene it is desirable that the feed should be rich in glycol component, i.e. the molar feed ratio of glycol-to-isobutylene should be in the range 10:1 to 100:1. These conditions are illustrated in the accompanying examples.

The C-4 hydrocarbon stream used as a reactant should preferably contain a significant quantity of isobutylene. Typically, the isobutylene concentration in said C-4 hydrocarbon mix should be in the range 1–50%. Other compounds commonly found in such a stream include, for example, isobutane, butene-1, 1,3-butadiene, n-butane, trans-butene-2, and cis-butene-2. Suitable feedstocks include C-4 raffinate streams, such as raffinate-1, and B—B streams from a butadiene plant. The accompanying examples illustrate the use of a typical raffinate-1.

The catalysts used to effect this reaction are preferably heteropoly acids. Preferably said heteropoly acids are bonded to an inert support, but they may also be solubilized in the reactants or products and used as homogeneous catalysts.

The heteropoly acids that are effective in the subject reaction comprise a class of acids formed by the condensation of two or more inorganic oxyacids. For example, phosphate and tungstate ions, when reacted in an acidic medium, are condensed to form 12-tungstophosphoric acid, a typical heteropoly acid (HPA) according to Equation 2:

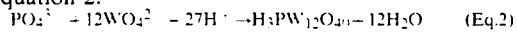

(Eq.2)

A wide variety of elements ranging from Group I to Group VIII can become the central atom of the HPA anion, or the heteroatom as it is called (P in the case of Eq. 2). The nature of the heteroatom is a governing factor which determines both the condensation structure and the physical properties of the HPA.

Atoms coordinated to the heteroatom via oxygens are called polyatoms (W in the case of Equation 2) and in most cases are any one of such limited species as molybdenum, tungsten, niobium and vanadium. In the case of molybdenum (Mo) as the polyatom, the nature of the heteroatoms, condensation ratios and chemical formulae of the corresponding HPA anions are summarized in Table I.

Anions containing the so-called Keggin structure have a condensation ratio of 1:12 and are the most typical of all HPA anions. Heteropoly acids with the Keggin structure, and their homologues, are generally the most readily available HPA's and the ones most commonly used in catalysis. The synthesis of these HPA's is well documented in the literature [see for example U.S. Pat. 3,947,332 (1976)].

TABLE I

| Typical heteropolymolybdate anions | | | |
|---|---|---|---|
| CONDENSATION RATIOS | | HETERO ATOMS (X) | CHEMICAL FORMULAS |
| 1:12 | Keggin structure | $P^{5+}, As^{5+}, Si^{4+}, Ge^{4+}$ | $[X^{n-}Mo_{12}O_{40}]^{-(8-n)}$ |
|  | Silverton structure | $Ce^{4+}, Th^{4+}$ | $[X^{4+}Mo_{12}O_{42}]^{8-}$ |
| 1:11 | Keggin structure (decomposition) | $P^{5+}, As^{5+}, Ge^{4+}, Si^{4+}$ | $[X^{n-}Mo_{11}O_{39}]^{-(12-n)}$ |
| 2:18 | Dawson structure | $P^{5+}, As^{5+}$ | $[X_2^{5-}Mo_{18}O_{62}]^{6-}$ |
| 1:9 | Waugh structure | $Mn^{4+}, Ni^{4+}$ | $[X^{4+}Mo_9O_{32}]^{6-}$ |
| 1:6 | Anderson structure | | |
|  | (A type) | $Te^{6+}, I^{7+}$ | $[X^{n-}Mo_6O_{24}]^{-(12-n)}$ |
|  | (B type) | $Co^{3+}, Al^{3+}, Cr^{3+}$ | $[X^{n-}Mo_6O_{24}H_6]^{-(6-n)}$ |
| 4:12 |  | $As^{5+}$ | $[H_4As_4Mo_{12}O_{52}]^{4-}$ |
| 2:5 |  | $P^{5+}$ | $[P_2Mo_5O_{23}]^{6-}$ |

In the case of separating isobutylene from a C4 hydrocarbon stream, suitable heteropoly acid catalysts may contain polyatoms selected from the group molybdenum, tungsten, niobium and vanadium, while the heteroatoms may be phosphorus, silicon, germanium, and arsenic. Preferably the heteroatoms are phosphorus or silicon. These heteropoly acids would likely have the Keggin structure, $H_{8-n}[XM_{12}O_{40}]$, where $X = P$ or $Si$, $M = Mo$ or $W$ and $n$ is an integer which is 4 or 5.

The preferred heteropoly acids for the practice of this invention include 12-molybdophosphoric acid, $H_3PMo_{12}O_{40}$, 12-tungstophosphoric acid, molybdosilicic acid, $H_4SiMo_{12}O_{40}$ and 12-tungstosilicic acid. Said acids are generally used as heterogeneous catalysts bonded to a suitable support.

The support should preferably comprise an inert compound. Compounds which may be employed are those containing elements of Group III and IV of the Periodic Table. Suitable compounds include the oxides of aluminum, silicon, titanium and zirconium or combinations thereof, e.g. alumina, silica (silicon dioxide), titania (titanium dioxide) and zirconia. Also suitable are carbon, ion-exchange resins, carbon-containing supports and silica-alumina clays including the montmorillonite clays. Good results were observed using $TiO_2$ as the support.

The inert support may be in the form of powders, pellets, spheres, shapes and extrudates. As will be demonstrated by the examples, the supports are preferably of high purity and high surface area.

The weight percent of heteropoly acid to Group III/Group IV support should be such that the concentration of the polyatom (Mo, W, Nb or V) in the formulated catalyst is in the range of 0.1 wt % to 30 wt %, although concentrations outside this range may also be employed. Where the heteropoly acid is, for example, 12-molybdophosphoric acid, supported on titania, a suitable quantity of molybdenum is 1-10 wt %. In the preparation of a tungstophosphoric acid-on-titania catalyst, on the other hand, the tungsten content may be 1-30 wt %.

The two-step separation of isobutylene from a C-4 rich hydrocarbon stream can be conducted batchwise, or in a continuous slurry bed reactor, or in a fixed bed, continuous flow reactor. For practical reasons a fixed bed process is preferred for both steps.

The principal glycol ether products produced in Step (I) of this process will depend primarily upon the choice of glycol coreactant. In the case of ethylene glycol, the addition of the C-4 hydrocarbon feedstock rich in isobutylene results in the formation of ethylene glycol mono-t-butyl ether (EGTBE). When the substrate is 1,2-propylene glycol, the addition of isobutylene results in the formation of 1-t-butoxy-2-propanol (PGTBE-20H) plus lesser amounts of 2-t-butoxy-1-propanol (PGTBE-10H). Generally, the majority monoalkyl glycol ether products are formed in accordance with the Markovnikov rules of addition to the double bond of the isobutylene substrate and involve the primary (rather than the secondary) hydroxyl group of the glycol substrate. Small quantities of 1,2-dibutoxypropane (PGDTBE) may be formed during the deetherification of PGTBE.

The first step in separation of isobutylene is preferably accomplished at a generally lower temperature than the second step. Etherification is generally conducted at temperatures of from about 60° to 160° C. The preferred range is 100° C. to 140° C. The deetherification can be accomplished at a temperature of from about 100° to 220° C. The a preferred temperature is from 160° to 200° C. The pressure can vary from 0 to 1000 psig. The preferred pressure for the deetherification step is as low as possible, e.g. from 0 to 300 psig. Optimum conditions may vary.

The resultant reaction mixture from the first step in the process (Step (1) in Eq. 1), the etherification reaction to give glycol mono-t-butyl ether, may comprise a single or bi-phase liquid product from which said glycol mono-t-butyl ether fractions may be recovered by the usual methods, including fractional distillation and liquid-liquid extraction, or via membrane technology. The resulting glycol mono-t-butyl ether, in crude or purified form is then, after possible dilution with additional glycol, fed in a second step (Step (2) in Eq. 1) to a deetherification reactor system also containing a heteropoly acid on an inert support catalyst. The regenerated isobutylene present in the effluent from the deetherification step may be easily recovered from unreacted glycol mono-t-butyl ether and glycol diluent by a simple stripping operation.

Typically the glycol mono-t-butyl ether intermediate is generated in up to about 5-10% concentration in the glycol-rich phase of the product effluent in the first, etherification step (Eq. 1). After recovery and dilution of said glycol mono-t-butyl ether in glycol diluent, the isobutylene is liberated in the second deetherification unit, also in up to 5-10% concentration.

These glycol ether and isobutylene concentrations are normally achieved in continuous processing at total liquid hourly space velocities (LHSV) of 1 to 5 under mild conditions.

Here LHSVs is defined as follows:

$$LHSV = \frac{\text{Volume Of Total Liquid Feed Run Through The Reactor Per Hour}}{\text{Volume of Catalyst in Reactor}}$$

Typically conversion of the isobutylene fraction in the C-4 hydrocarbon stream to glycol mono-t-butyl ether during the etherification step is 10-90% per pass, using continuous unit equipment; conversion of said glycol mono-t-butyl ether, diluted with glycol, to isobutylene during deetherification is also typically 10-90%.

The accompanying Examples illustrate:

1) The etherification of the isobutylene fraction of a typical raffinate-1-stream to propylene glycol t-butyl ether by reaction with a 1,2-propylene glycol over a 12-tungstophosphoric acid-on-titania catalyst (Example 1, Step (1) in Eq. 3) here the highest isobutylene conversion is achieved at 120° C., using a LHSV of 1.2; the propylene glycol t-butyl ether concentration in the PG-rich phase of the effluent product is ca. 4%, the 2-OH/1-OH isomer distribution is ca. 7:1.

2) Deetherification of the propylene glycol t-butyl ether product from Example 1 to give pure isobutylene plus propylene glycol (Example 2). Here the glycol ether feed is diluted with 1,2-propylene glycol and the catalyst is again 12-tungstophosphoric acid-on-titania. Operating at 180° C., the propylene glycol t-butyl ether conversion per pass is ca. 70%, Eq. 3, Step (2).

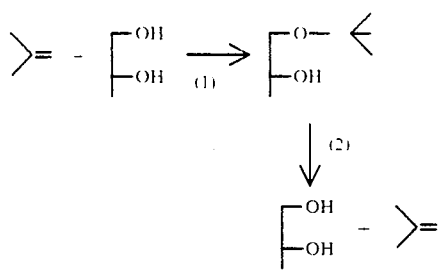

(Eq. 3)

The examples which follow illustrate the two-step separation of isobutylene from a raffinate-1 feedstock using a heteropoly acid on titania. The examples are only intended as a means of illustration and it should be understood that the invention is not meant to be limited thereby.

EXAMPLE A

To a 250 cc sample of titania tablets (1/8" diameter surface area 158 m$^2$/g, bulk density 1.03 g/cc) was added a solution of 80.0 g of 12-tungstophosphoric acid in 150 cc of distilled water. The mixture was first stirred to absorb the liquid into the pores of the solid and then excess liquid was removed by slow rotary evaporation. The solid tablets were calcined in a stream of nitrogen at 150° C. for 1 hour and at 350° C. for 2 hours.

Analysis of the finished catalyst was as follows:
Tungsten—15.8%
Phosphorous—0.2%
Water—0.2%
Acidity—0.52 meq/g

EXAMPLE 1

To a 50 cc capacity, plug flow, continuous reactor fitted with temperature and pressure controls, was charged 40 cc of a 12-tungstophosphoric acid-on-titania catalyst, prepared by the method of Example A. A mixture of raffinate-1 containing ca. 12.7% isobutylene, plus 1,2-propylene glycol, were then fed separately to the reactor at rates of 16 cc/hr and 32 cc/hr respectively. The reactor was heated to temperature and a back pressure of 300 psi was maintained. After allowing the system to reach equilibrium, by operating 4–6 hours, the effluent samples were collected in 316 ss pressure bombs. Each effluent comprised two layers. They were then separated and analyzed.

The procedure was repeated for four different operating temperatures (60°–120° C.). Analyses of the on-line product mixtures are summarized in Table II.

EXAMPLE 2

To a 50 cc capacity, plug flow, continuous reactor fitted with temperature and pressure controls, was charged 40 cc of a 12-tungstophosphoric acid-on-titania catalyst, prepared by the method of Example A. Propylene glycol mono-t-butyl ether, prepared by the method of Example 1, and diluted with 1,2-propylene glycol, was then fed to said reactor at a rate of 40 cc/hr. The reactor was heated to temperature and a back pressure of 100 psi was maintained. After allowing the system to reach equilibrium overnight, the effluent samples were collected in 316 ss pressure bombs and analyzed.

This procedure was repeated for four different operating temperatures (100°–180° C.). Analyses of the on-line product mixtures are summarized in Table III.

TABLE II

PG t-Bu Ether From PG + C$_4$H$_8$

| | | | | PRODUCT COMPOSITION (%) | | | | | | | | | |
|---|---|---|---|---|---|---|---|---|---|---|---|---|---|
| | | | | Top Layer | | | | | | Bottom Layer | | | |
| | | Flow | | C-4 | | C-4' | | | | PGTBE | | | |
| Ex. | Catalyst | Temp. (°C.) | Rates (cc/hr) | Sample # | ISO | n | T-2 | 1— | ISO | C-2 | C-4's | 2-OH | 1-OH | PG |
| 1 | A | | | FS | 10.8 | 31.6 | 17.5 | 12.2 | 12.7 | 13.4 | | | | |
| | | 60 | 16/32 | 1 | 11.1 | 33.6 | 17.3 | 11.9 | 11.2 | 13.3 | 8.3 | 0.8 | 0.2 | 89.3 |
| | | | | 2 | 11.1 | 33.0 | 17.4 | 12.1 | 12.1 | 13.3 | 8.5 | 0.8 | 0.2 | 89.5 |
| | | 80 | | 3/3A | 11.2 | 33.1 | 17.2 | 12.0 | 10.6 | 13.2 | 9.0 | 1.5 | 0.3 | 88.6 |
| | | | | 4/4A | 10.8 | 32.8 | 17.3 | 12.2 | 10.8 | 13.4 | 9.8 | 1.4 | 0.3 | 87.2 |
| | | 100 | | 5 | | | | | a | | 8.1 | 2.3 | 0.4 | 87.4 |
| | | | | 6 | 11.4 | 34.2 | 17.8 | 12.3 | 9.2 | 13.4 | 7.1 | 2.0 | 0.4 | 89.1 |
| | | 120 | | 7 | 11.6 | 35.0 | 18.2 | 12.6 | 7.1 | 13.9 | 10.0 | 3.6 | 0.5 | 84.0 |
| | | | | 8 | 11.5 | 34.8 | 18.2 | 12.5 | 7.4 | 13.9 | 8.4 | 3.4 | 0.5 | 85.8 |

*Insufficient sample for analysis

TABLE III

PG t-Bu ETHER TO PG + C$_4$H$_8$

| | | | Flow | | PRODUCT COMPOSITION (%) | | | | |
|---|---|---|---|---|---|---|---|---|---|
| | | Temp. | Rate | Sample | | PGTBE | | PG | |
| Ex. | Catalyst | (°C.) | (cc/hr) | # | C$_4$H$_8$ | 2-OH | 1-OH | DTBE | PG |
| 2 | A | | | FS-1 | | 9.3 | . | | 90.0 |
| | | 100 | 40 | 1 | 0.8 | 7.5 | 0.7 | 0.1 | 88.5 |
| | | | | 2 | 0.8 | 7.7 | 0.7 | 0.1 | 88.2 |
| | | 120 | 40 | 3 | 1.4 | 6.8 | 0.8 | 0.1 | 87.7 |
| | | | | 4 | 1.5 | 6.7 | 0.8 | 0.1 | 86.7 |
| | | 150 | 40 | 5 | 2.5 | 5.2 | 0.8 | 0.1 | 87.1 |
| | | | | 6 | 2.6 | 5.2 | 0.8 | 0.1 | 86.7 |
| | | 180 | 40 | 7 | 4.3 | 2.8 | 0.5 | 0.1 | 82.7 |
| | | | | 8 | 4.2 | 2.8 | 0.5 | 0.1 | 83.7 |

What is claimed is:

1. A two-step method for separating isobutylene from a C-4 hydrocarbon fraction comprising:

a) Contacting the C-4 fraction containing isobutylene with a glycol in the presence of a catalyst comprising a heteropoly acid on an inert support at a temperature of about 60° to 160° C. thereby reacting the isobutylene with the glycol to yield a glycol mono-t-butyl ether, and subsequently b) reacting the glycol mono-t-butyl ether over the heteropoly acid on an inert support at a temperature between 150° C. to 220° C. to produce the separated isobutylene.

2. The method of claim 1 wherein the glycol is selected from the group consisting of ethylene glycol and 1,2-propylene glycol.

3. The method of claim 1 wherein the heteropoly acid is represented by the structure:

$$H_n[xM_{12}O_{40}]$$

where $x = P$ or $Si$, $M = Mo$ or $W$ and $n$ is an integer which is 4 or 5.

4. The method of claim 1 wherein the catalyst is a heteropoly acid from the class of acids formed by the condensation of two or more inorganic oxyacids.

5. The method of claim 1 wherein the heteropoly acids are selected from the group consisting of 12-tungstophosphoric acid, 12-molybdophosphoric acid, 12-tungstosilicic acid and 12-molybdosilicic acid.

6. The method of claim 1 wherein the inert support is an oxide selected from the group consisting of titanium dioxide, alumina and silica.

7. The method of claim 3 wherein the wt % concentration of M in the formulated catalyst is in the range of 0.1 to 30 wt %.

8. The method of claim 3 wherein the heteropoly acid is 12-tungstophosphoric acid, the support is titanium dioxide and the tungsten content in the formulated catalyst is in the range of 1 to 30 wt %.

9. The method of claim 1 wherein the molar ratio of glycol to isobutylene fraction in the C-4 feed during formation of the desired glycol t-butyl ether is in the range of 10:1 to 100:1.

10. The method of claim 1 wherein the temperature range in the first step is from about 100° to 140° C.

11. The method of claim 1 wherein the temperature range in the second step is from about 160° to 200° C.

12. The process of claim 1 wherein the operating pressure can vary from zero to 1000 psig.

* * * * *